(12) United States Patent
Ogawa (10) Patent No.: US 6,855,514 B2
(45) Date of Patent: Feb. 15, 2005

(54) METHOD FOR DETECTING PRESENCE OF MICROORGANISMS, AND QUANTITIES OF MICROORGANISMS

(76) Inventor: Hiroyuki Ogawa, 4-16-306, Nishikicho 2-chome Aoba-ku, Sendai-shi, Miyagi 980-0012 (JP)

( * ) Notice: Subject to any disclaimer, the term of this patent is extended or adjusted under 35 U.S.C. 154(b) by 46 days.

(21) Appl. No.: 09/897,105

(22) Filed: Jul. 3, 2001

(65) Prior Publication Data

US 2001/0039033 A1 Nov. 8, 2001

Related U.S. Application Data

(62) Division of application No. 09/213,872, filed on Dec. 17, 1998, now abandoned.

(30) Foreign Application Priority Data

Dec. 18, 1997 (JP) .............................. 9-365342

(51) Int. Cl.⁷ ................................................ C12Q 1/04
(52) U.S. Cl. ...................................... 435/34; 435/287.5
(58) Field of Search .............................. 435/34, 287.5, 435/297.1; 202/178; 204/429; 422/86

(56) References Cited

U.S. PATENT DOCUMENTS

| | | | | |
|---|---|---|---|---|
| 4,513,280 A | * | 4/1985 | Hannan et al. ............. | 205/778 |
| 4,945,060 A | * | 7/1990 | Turner et al. ............... | 435/291 |
| 5,494,640 A | * | 2/1996 | Simon et al. ............ | 422/82.05 |
| 5,851,611 A | * | 12/1998 | Guttag ...................... | 428/35.7 |
| 5,858,769 A | * | 1/1999 | DiGuiseppi et al. ..... | 435/287.3 |

FOREIGN PATENT DOCUMENTS

| | | | |
|---|---|---|---|
| JP | 60-130398 | | 7/1985 |
| JP | 02-057198 | | 2/1990 |
| JP | 2-154697 | * | 6/1990 |
| JP | 07-008294 | | 1/1995 |
| WO | WO 93/15402 | * | 8/1993 |

* cited by examiner

*Primary Examiner*—Ralph Gitomer
(74) *Attorney, Agent, or Firm*—Snider & Associates; Ronald R. Snider (57) ABSTRACT

Fast microbial detection is accomplished without an indicator interfering with microorganism growth, without a culture medium degrading the performance of an indicator and without a color of test sample adversely effecting th micro-bial detection process. A container has a portion which accommodates a fluid culture medium, and has a portion which accommodates a $CO_2$ indicator. A $CO_2$ gas-permeable membrane isolates the $CO_2$ indicator from the fluid culture medium. The test sample is added in the fluid culture medium and then the container is sealed. The determination of the presence of microorganisms is accomplished by verifying a color change of a $CO_2$ indicator. The quantity of mircoorganisms is determined by measuring time from when the container is sealed until an indicator portion has a color change.

3 Claims, 5 Drawing Sheets

METHOD FOR DETECTING PRESENCE OF MICROORGANISMS, AND QUANTITIES OF MICROORGANISMS

This application is a Divisional of application Ser. No. 09/213,872 filed on Dec.17, 1998 now abandoned.

This application claims the priority of Japanese Patent Application No. 9-365,342, filed on Dec.18, 1997, which is incorporated herein by reference.

TECHNICAL FIELD

This invention relates to a method for detecting microorganisms that produce $CO_2$ gas as a consequence of the growth in a culture medium, a method for identifying the quantities of microorganisms, microbial detection tools, a microbial detection system, and a microbial growth time measuring system.

BACKGROUND ART

For detecting the presence of such microorganism in food as *Escherichia coli, Staphylococcus aureus,* Vibrio or the like, that causes food poisoning, a method that has been widely practicing involves adding a test sample in a fluid culture medium with a color-turning indicator mixed in it. The determination of whether or not a test sample is contaminated with microorganisms is accomplished by observing the indicated color response of a mixture after a mixture is incubated at suitable temperature for certain period of time.

However, with the commonly used technique, it requires longer time to detect the presence of microorganisms with a color response since the choice of indicator is constrained to avoid adverse effect on the growth of microorganisms when an indicator is mixed with a liquid culture medium. It is also known that some indicators interfere the growth of microorganisms and in some cases a culture medium degrades the performance of an indicator when they are mixed together. Furthermore, by observing a color change of a mixture, the determination of microbial detection becomes harder and a wrong result might be led if a color of a test sample itself is dark or deep.

The objective of the present invention is to provide a simple, efficient, fast and reliable microbial detection by;
(a) a method for detecting the presence of microorganisms,
(b) a method for identifying the quantities of microorganisms,
(c) self-contained microbial detection tools,
(d) a microbial detection system, and
(e) a microbial growth time measuring system, without an indicator interfering the growth of microorganisms, without a culture medium degrading the performance of a indicator and without a color of a test sample adversely effecting the process of microbial detection, while providing a solution to the commonly used technique to overcome its drawbacks.

DISCLOSURE OF THE INVENTION

To achieve said objectives, a microbial detection method of the present invention is characterized by the whole arrangement for determining the presence of microorganisms with a color response of a $CO_2$ indicator which is accommodated in a container capable of sealing together with a mixture of a test sample and a fluid culture medium that supports the growth of microorganisms, and is isolated from said mixture by a $CO_2$ gas-permeable membrane.

A color-turning $CO_2$ indicator is preferably a mixture solution of a pH color indicator and a pH shifting substance reactive to $CO_2$ gas such as a mixture solution of sodium hydroxide (NaOH) and thymolphthalein or a mixture solution of sodium hydroxide (NaOH) and phenolphthalein, for example, but an indicator can also be a solution of calcium hydroxide ($Ca(OH)_2$) or a solution of substance containing heme such as hemoglobin, red blood cell or blood. Moreover, an indicator can also comprise such compound, called by common name, as Methyl Violet, Methyl Orange, Congo Red, Methyl Red, Bromthymol Blue, Phenol Red, Cresol Red, Thymol Blue, or litmus.

A $CO_2$ gas-permeable membrane separating a culture medium is preferably ion-impermeable film which isolates a $CO_2$ indicator from a culture medium completely except gaseous form. As a $CO_2$ gas-permeable membrane, non-oriented polypropylene film, oriented polypropylene film, low density polyethylene film, high density polyethylene film or as such can be used, for example. Moreover, silicon rubber film or polyalkylsulfone film, which exhibits the same performance characteristics on any spot of a sheet, or polytetrafluoroethylene film or polysulfone film, which has pores, or compound film of polypropylene and silicon, or compound film of polypropylene and polyalkylsulfone, can also be used as a $CO_2$ gas-permeable membrane.

Film which has the characteristic to permeate $CO_2$ gas at higher pressure, is utilized as a $CO_2$ gas-permeable membrane, to keep certain level of $CO_2$ density inside a culture medium portion. To detect those microorganisms such as *Neisseria gonorrhoeae, Neisseria meningitidis* or *Campylobacter*, that needs 5~10% of $CO_2$ density for the growth, the required $CO_2$ density is kept inside of a medium portion when a film sheet of such characteristic is used, and the $CO_2$ gas given off by the process of microbial growth build up pressure until reaching to the threshold level so that only excess amounts of $CO_2$ permeate the membrane and react on a color-tuning $CO_2$ indicator. A test sample can be either liquid type or solid type.

The method for detecting the presence of microorganisms, of the present invention is characterized by the following. When a test sample mixed in a culture medium contains microorganisms, microorganisms grow in a medium, using and breaking down nutrients, and the $CO_2$ gas is given off as a consequence of microbial metabolism. The $CO_2$ gas given off by microorganisms react on a $CO_2$ indicator and turn its color. Based on a color response of a $CO_2$ indicator, the presence of microorganisms is determined. Since a $CO_2$ indicator actively reacts on the increased amounts of $CO_2$ gas, the microbial detection can be done efficiently and rapidly. Further more, a culture medium and a $CO_2$ indicator are isolated by a $CO_2$ gas-permeable membrane so that ingredients of a $CO_2$ indicator do not cause any adverse effects on nutrients required for the microbial growth, a culture medium does not degrade the performance of a $CO_2$ indicator and the color of a test sample does not interfere the observation of a color change indicated by a $CO_2$ indicator. Therefore, a result of microbial detection is more reliable.

The method for identifying the quantities of microorganisms, of the present invention is characterized by the following. Using a container which comprises a medium portion to have a fluid culture medium for supporting the growth of microorganisms and an indicator portion to have a color-turning $CO_2$ indicator for detecting the presence of microorganisms and inside of which an indicator portion is isolated from a medium portion by a $CO_2$ gas-permeable membrane, a test sample containing microorganisms is mixed in a culture medium and a container is sealed entirely from outside atmosphere. The reaction time is measured, starting from the moment when a container is sealed until the moment when a color of a $CO_2$ indicator is turned into the predetermined color. The initial quantities of microorganisms are obtained by comparing the measured time against contents of the table which holds pre-collected time data on each microorganism species of known initial quantities in known amount of sample.

When surrounding environmental conditions are kept constant, a reaction time took for a $CO_2$ indicator to turn its color has certain relationship and correlates to the quantities of microorganisms grown and increased in a medium during the test interval. A test sample containing more microorganisms initially takes shorter time to react on a $CO_2$ indicator, and less microorganisms take longer. The initial quantities of microorganisms in a sample under test is estimated and obtained by comparing the measured time against contents of the table which holds pre-collected time data on each microorganism species of known initial quantities in known amount of a sample. For this application, a high species selective culture medium is desirable to be used.

The microbial detection indicator tool of the present invention is characterized by a color-turning $CO_2$ indicator enclosed by a transparent bag of $CO_2$ gas-permeable membrane which isolates an indicator from a fluid culture medium containing a sample.

The microbial detection indicator tool of the present invention has very simple structure. It is used by dipping itself in a sample containing culture medium that is sealed from outside. The presence of microorganisms is detected by observing a color response of a $CO_2$ indicator inside of the transparent bag. This microbial detection indicator tool can be utilized for previously described method for detecting microorganisms and the method for identifying the quantities of microorganisms, and brings the expected effect and result.

The microbial detection container tool of the present invention is characterized by comprising a medium portion to have a fluid culture medium for supporting the growth of microorganisms, an indicator portion to have a color-turning $CO_2$ indicator for detecting the presence of microorganisms, a $CO_2$ gas-permeable membrane to isolate an indicator portion from a medium portion, and a transparent container accommodating an indicator, a membrane and a medium and having a capability of sealing entirely from outside atmosphere. A container can be entirely or partly transparent as long as an indicator portion can be verified from outside.

Using a microbial detection container tool of the present invention, the determination of the presence of microorganisms is accomplished by observing a color response of a $CO_2$ indicator after a test sample is mixed in a culture medium and then a container is sealed. By keeping this container tool airtight before being put in use, it can be prevented for this tool to be less performance effective since an indicator does not react on $CO_2$ in atmosphere. This microbial detection container tool can be utilized for previously described method for detecting microorganisms and method for identifying the quantities of microorganisms, and brings the expected effect and result.

The microbial detection system of the present invention is characterized by comprising: (a) a loading portion for a microbial detection container tool which comprises a medium portion to have a fluid culture medium for supporting the growth of microorganisms, an indicator portion to have a color-turning $CO_2$ indicator for detecting the presence of microorganisms, a $CO_2$ gas-permeable membrane to isolate an indicator portion from a medium portion, and a container accommodating an indicator, a membrane and a medium, having a transparent portion for verifying an indicator portion from outside, and having a capability of sealing entirely from outside atmosphere;

(b) a sensor to detect a color change of a $CO_2$ indicator in a container placed on a loading portion, and to send the microorganism detection signal to an alarm; and (c) an alarm to inform the detection of microorganisms, according to the microorganism detection signal provided by a sensor.

Using a microbial detection system of the present invention, after a test sample is mixed in a culture medium and a microbial detection container tool is sealed, the container is placed on a loading portion of a detection system. A sensor detects the presence of microorganisms by monitoring a color response of a $CO_2$ indicator and sends the signal to an alarm which informs the microorganism detection. Because of this arrangement, a $CO_2$ indicator does not have to be observed all the time.

The microbial growth time measuring system of the present invention is characterized by comprising:

(a) a loading portion for a microbial detection container tool which comprises a medium portion to have a fluid culture medium for supporting the growth of microorganisms, an indicator portion to have a color-turning $CO_2$ indicator for detecting the presence of microorganisms, a $CO_2$ gas-permeable membrane to isolate an indicator portion from a medium portion, and a container accommodating an indicator, a membrane and a medium, having a transparent portion for verifying an indicator portion from outside, and having a capability of sealing entirely from outside atmosphere;

(b) a sensor to detect a color change of a $CO_2$ indicator in a container placed on a loading portion, and to send the microorganism detection signal to a timer; and (c) a timer to measure the time, starting from the moment when a container containing a test sample is placed on a loading portion until the moment when the microorganism detection signal is received from a sensor.

Using a microbial growth time measuring system of the present invention, after a test sample is mixed in a culture medium and a microbial detection container tool is sealed, a container is placed on a loading portion of a system. As soon as a container is placed, a timer is triggered to be started. The initial quantities of microorganisms in a sample under test is obtained by comparing the measured time against contents of the table which holds pre-collected time data on each microorganism species of known initial quantities in known amount of a sample. For this application, a high species selective culture medium is desirable to be used.

When a method for detecting microorganisms, a method for identifying quantities of microorganisms, a microbial detection tool, a microbial detection system, or a microbial growth time measuring system of the present invention is applied, fast microbial detection can be accomplished, using an indicator sensitive to an amount increase of $CO_2$ gas, without an indicator interfering the growth of microorganisms, without a culture medium degrading the performance of a indicator and without a color of test sample adversely effecting the process of microbial detection, since a $CO_2$ indicator is isolated by a $CO_2$ gas-permeable membrane from a culture medium supporting the growth of microorganisms.

BRIEF DESCRIPTION OF THE DRAWINGS

(A) simplified figure of first form of application: a microbial detection tool (B) simplified figure of second form of application: a microbial detection tool (C) simplified figure of third form of application: a microbial detection tool (D) simplified figure of fourth form of application: a microbial detection tool (E) simplified figure of fourth form of application: detailed breakdown of a microbial detection tool (F) simplified figure of fifth form of application: a microbial detection tool FIG. 2 is simplified diagram of a microbial detection system used a microbial detection tool of first form that the present invention is applied to;

(A) Simplified figure showing a method for detecting microorganisms, using a microbial detection tool in first form of application (B) Bottom view of a $CO_2$ gas-permeable membrane at a test started (C) Bottom view of a $CO_2$ gas-permeable membrane when precipitates started to settle

(A) Simplified diagram (B) Graph showing microbial detection process; and

FIG. 5 shows simplified diagram of a microbial growth time measuring system used a microbial detection tool in fifth form that the present invention is applied to.

BEST MODE FOR CARRYING OUT THE INVENTION

Figure 1:
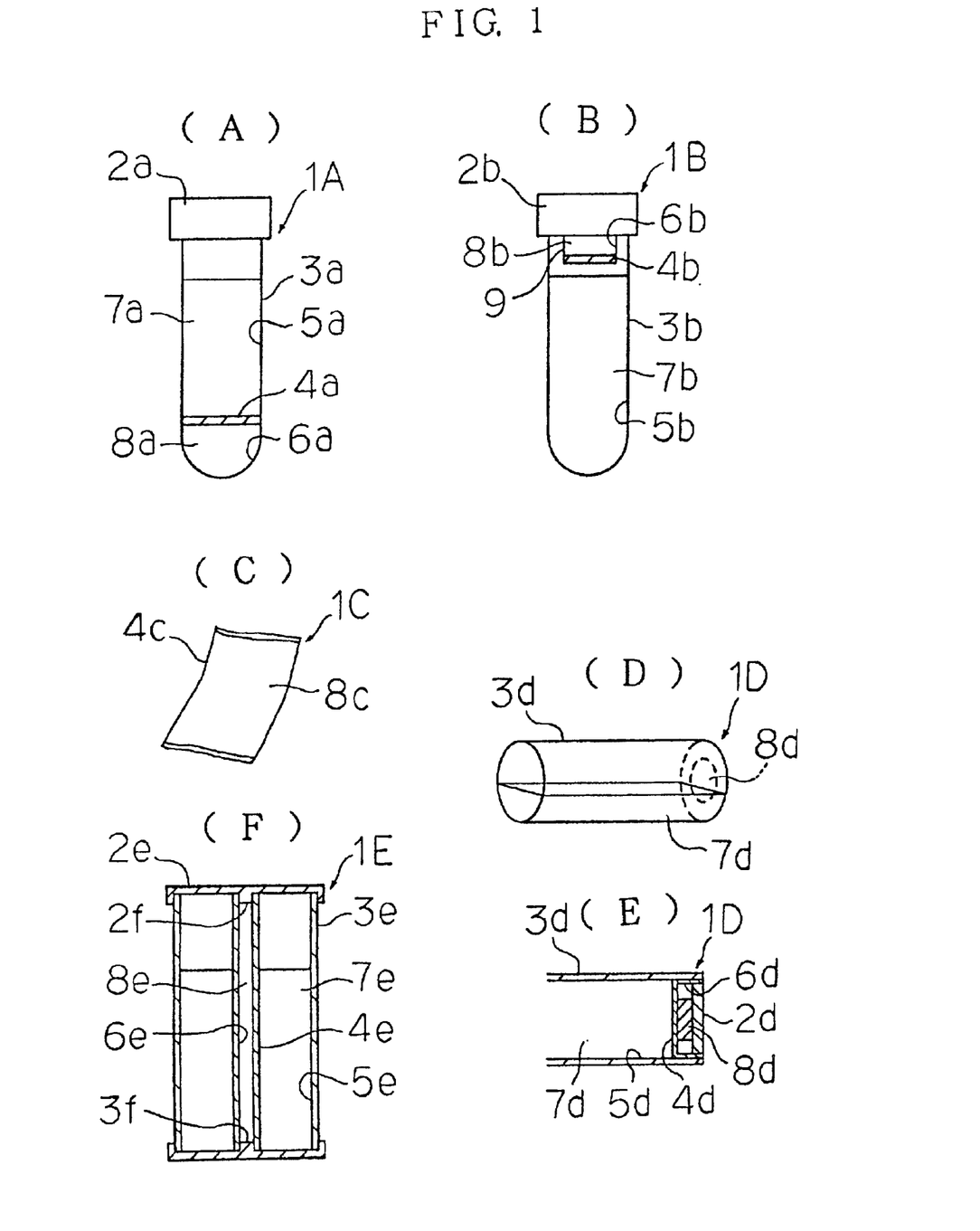
FIG. 1 shows some applications of a microbial detection tool of the present invention.

Using figures, some applications of the present invention are described as follows. FIG. 1 shows first form of application of the present invention. As FIG. 1(A) shows, a microbial detection container tool 1A is a transparent container 3a capable of keeping inside airtight by a cap 2a, inside of which a $CO_2$ gas-permeable membrane 4a isolates a $CO_2$ indicator portion 6a from a fluid culture medium portion 5a. A $CO_2$ gas-permeable membrane 4a is transparent polypropylene film which isolates a culture medium 7a. A fluid culture medium portion 5a is located at upper side and accessible by an opening and a $CO_2$ indicator portion 6a is located at lower side of a container 3a. A $CO_2$ indicator portion 6a accommodates a $CO_2$ indicator 8a and is separated by a $CO_2$ gas-permeable membrane 4a.

A $CO_2$ indicator 8a is a mixture solution of sodium hydroxide (NaOH) and thymolphthalein. Sodium hydroxide reacts on $CO_2$ gas and produces sodium carbonate. ($2NaOH+CO_2 \rightarrow Na_2CO_3+H_2O$) At the same time, pH shifts toward neutral from alkaline. Thymolphthalein has a color transition range of pH9.3~10.5 and becomes blue when pH is greater than 10.5, and colorless when pH is less than 9.3.

To achieve this, a $CO_2$ indicator 8a is prepared by adding a few drops of thymolphthalein into approximately 50 ml of deionized water and adding sodium hydroxide to the solution until color of solution becomes deep blue. To use the solution as a $CO_2$ indicator 8a, a ratio of sodium hydroxide and thymolphthalein may be adjusted for the best detection of microorganisms. When sodium hydroxide of a $CO_2$ indicator 8a reacts on $CO_2$ gas, a color of a $CO_2$ indicator becomes colorless from deep blue. Instead of thymolphthalein, phenolphthalein can be used. In case of phenolphthalein, the color transition of pH range is located more closer to neutral so that sensitivity becomes less than that of thymolphthalein, but it is more stable as a $CO_2$ indicator. When sodium hydroxide reacts on $CO_2$ gas, a color of a $CO_2$ indicator comprising phenolphthalein becomes colorless from pink.

Figure 2:
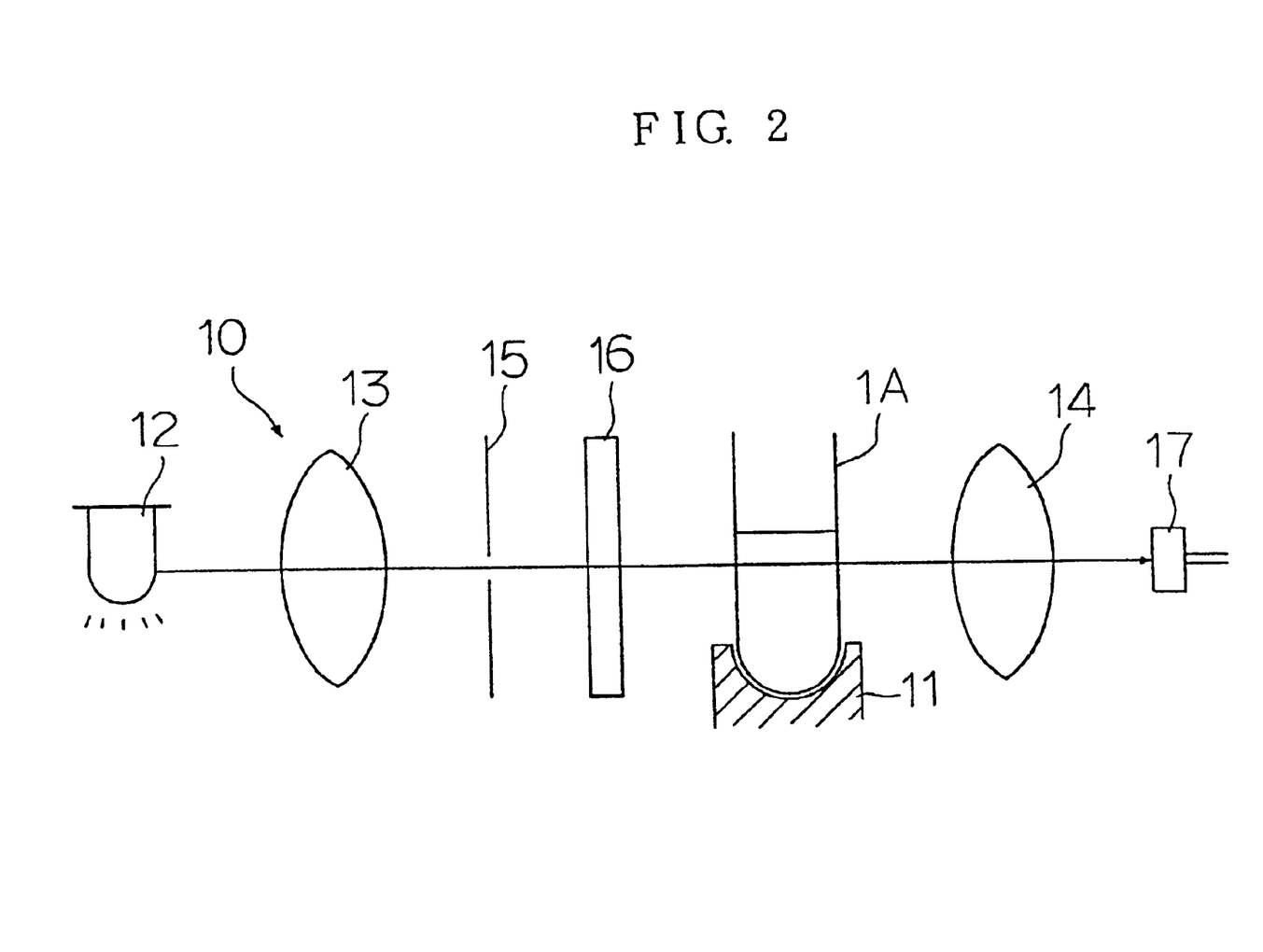

As FIG. 2 shows, a microbial detection system 10 using a microbial detection container tool 1A comprises a loading portion 11 for a microbial detection container tool 1A, a light source 12, lenses 13, 14, a slit 15, a color filter 16, a sensor 17 and an alarm (not shown in the figure). Light from a light source 12 passes through a lens 13, a slit 15, a color filter 16 a $CO_2$ indicator 8A of a microbial detection container tool 1A, and a lens 14, and then is detected by a sensor 17. A sensor 17 picks up a color response of a $CO_2$ indicator 8a of a microbial detection container tool 1A placed on a loading portion 11, and then sends the microorganism detection signal to an alarm. An alarm informs the presence of microorganisms, according to the microorganism detection signal received from a sensor 17.

When a microbial detection container tool 1A shown in FIG. 1(A) is used for microbial detection, a test sample is mixed in a fluid culture medium 7a which is accommodated in a container 3a, inside of which a $CO_2$ gas-permeable membrane 4a isolates a $CO_2$ indicator 8a from a fluid culture medium 7a and then a container 3a is sealed airtight. A culture medium 7a can be of any type and can be used without considering pH or adverse effect which could be caused by a $CO_2$ indicator 8a. A medium also can be adjusted for the best suitable nutrient condition for specific microorganism in a target to grow, and can be made for more sensitive detection.

If a part of foodstuffs is contaminated with biologically active agents such as bacteria, for instance, the microorganisms grow, using and breaking down nutrients in a fluid culture medium 7a and produce $CO_2$ gas as a consequence of the growth if such a test sample is mixed in a fluid culture medium 7a. When microorganisms produce $CO_2$ gas, $CO_2$ react on a $CO_2$ indicator 8a and cause a color response. Therefore, by observing and verifying a color of a $CO_2$ indicator 8a in a $CO_2$ indicator portion 6a, the presence of microorganisms can be determined and the presence is detected whenever the color turned into colorless from deep blue.

A $CO_2$ indicator 8a contains sodium hydroxide which actively reacts on $CO_2$ gas produced by microorganisms so that detection sensitivity is much higher than that of mere pH indicator and a color response is fast. Especially when thymolphthalein is used for a $CO_2$ indicator 8a, an indicator has high detection sensitivity and detects the presence of microorganisms in short time since it has higher color transition range of pH9.3~10.5 and changes its color with smaller amount of reaction caused by sodium hydroxide.

A culture medium 7a is isolated from a $CO_2$ indicator 8a by a $CO_2$ gas-permeable membrane 4a so that a $CO_2$ indicator 8a does not cause any adverse effect on nutrient for microorganisms to grow. For this reason, even if substance that is a poison to microorganisms and severely damages the growth is used for a $CO_2$ indicator 8a, reliable microbial detection can be accomplished. For the same reason, pH of a culture medium 7a does not cause any effect on pH of a $CO_2$ indicator 8a and also reliable microbial detection can be accomplished with no adverse effect on a color response and no degradation of a indicator that could be caused by a culture medium without a membrane. By keeping this container tool airtight before being put in use, it can be prevented for a $CO_2$ indicator 8a to be less performance effective since an indicator does not react on $CO_2$ in atmosphere.

Furthermore, a choice of substance for a $CO_2$ indicator 8a, a ratio of sodium hydroxide and thymolphthalein and density of a $CO_2$ indicator 8a may be altered to have the best sensitivity for the microbial detection.

As FIG. 2 shows, when a microbial detection system 10 is used, a container 3a is placed on a loading portion 11 after a test sample is mixed in a culture medium 7a of a microbial detection container tool 1A and a container 3a is sealed. While surrounding environment conditions such as temperature are kept constant, the determination of the presence of microorganisms in a test sample is accomplished by sounding an alarm which is activated by a sensor 17 detecting a color response. For this arrangement, a $CO_2$ indicator 8a does not have to be observed all the time.

Both concept and structure of a microbial detection container tool 1A are quite simple and a color response of a $CO_2$ indicator 8a can be verified even by the naked eye so that the microbial detection automated by a microbial detection system 10 becomes also simple and reliable. Therefore, unlike the microbial detection system of the prior art, a microbial detection system 10 is highly reliable and has less chance of having false detections. A microbial detection system 10 is so simple that the system is very cost effective to be built.

Figure 3:
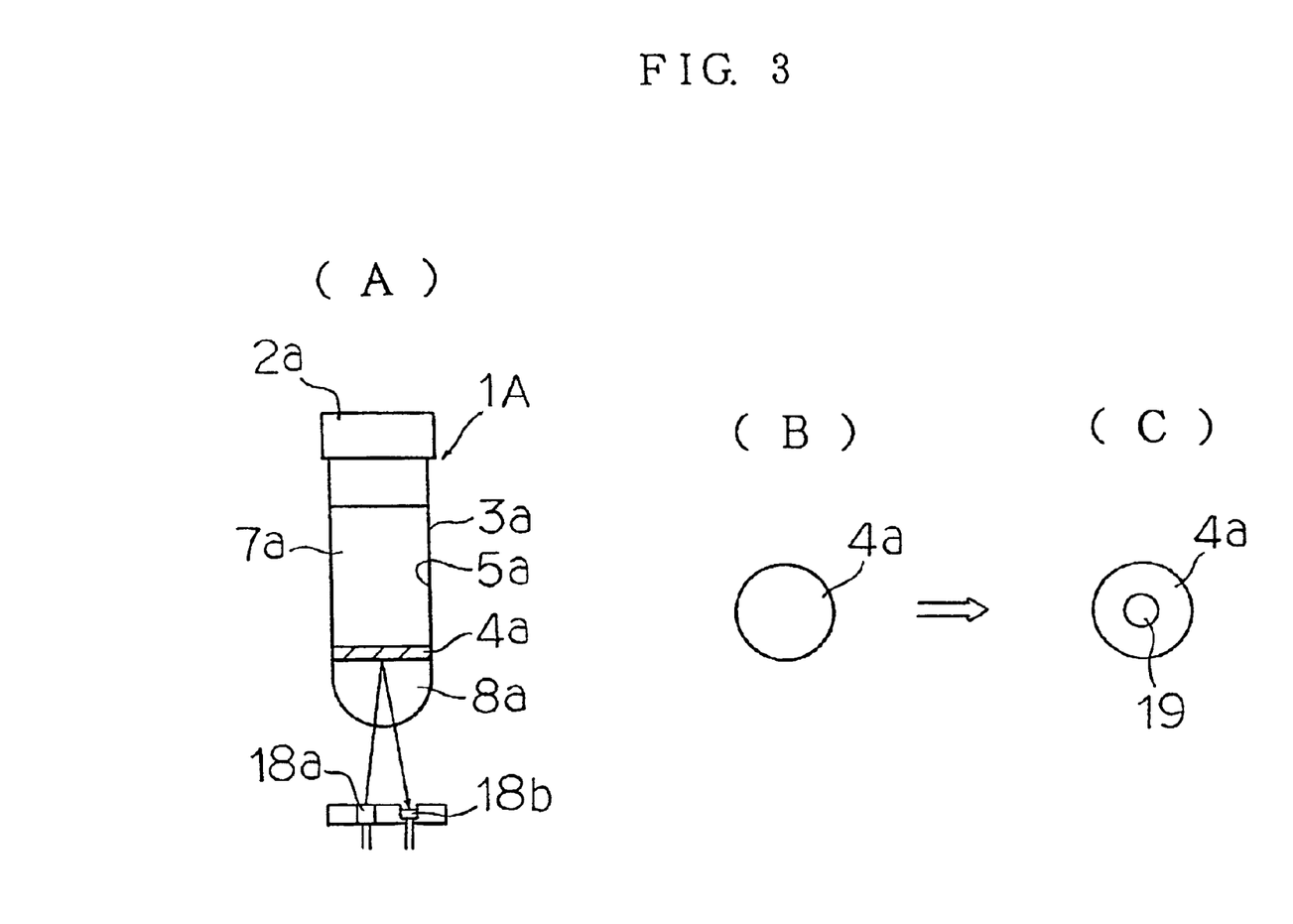
FIG. 3 shows some applications of the present invention.

Furthermore, like FIG. 3 shows, a solution of calcium hydroxide can be used as a $CO_2$ indicator 8a while using a $CO_2$ gas-permeable membrane 4a of black color. In addition to that, as FIG. 3 (A) shows, a light source 18a is located at a place lower than the bottom of a container 3a, lighting up a $CO_2$ gas-permeable membrane 4a. A sensor 18b detects reflected light and sends the microorganism detection signal to an alarm (not shown in the figure) informing the presence of microorganisms.

In this case, calcium hydroxide reacts on $CO_2$ gas produced by microorganisms as a consequence of microbial metabolism, $(Ca(OH)_2+CO_2 \rightarrow CaCO3+H_2O)$. White or milky precipitates of calcium carbonate are easier to be observed against a black $CO_2$ gas-permeable membrane 4a behind them. (Refer to FIGS. 3(B), (C)) A sensor picks up the reflected light as precipitates 19 increase and sends the microorganism detection signal to an alarm which informs the presence of microorganisms.

Figure 4:
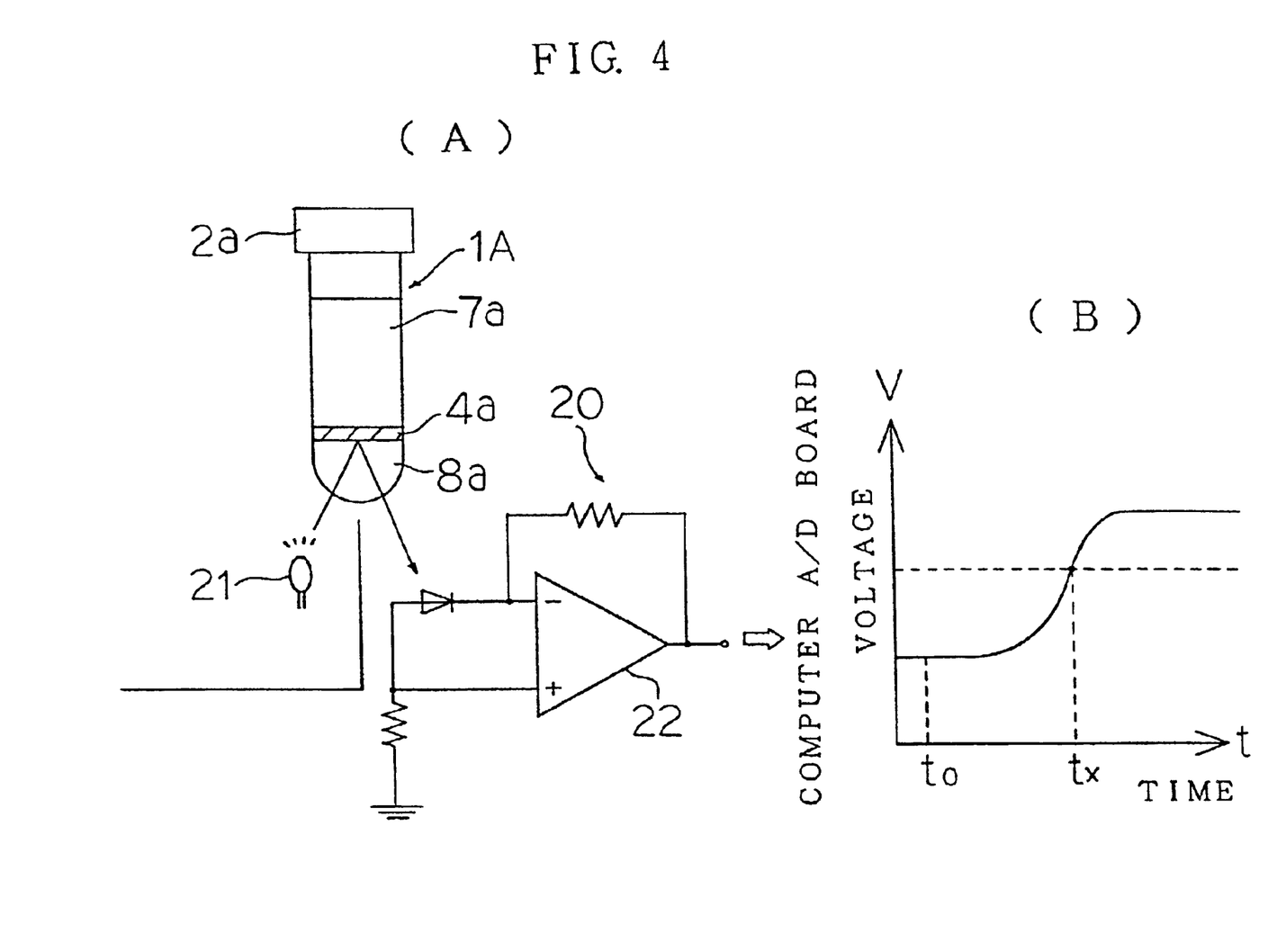
FIG. 4 is a microbial detection system used a microbial detection tool in FIG. 3.

As FIG. 4(A) shows, a microbial detection system 20 using a microbial detection container tool 1A comprises a loading portion for a microbial detection container tool 1A, a light source 21, a sensor, an analog amplifier circuit 22, an analog to digital (A/D) converter, a computer and an alarm. A light source 21 lights up a $CO_2$ gas-permeable membrane 4a and precipitates caused by reaction of a $CO_2$ indicator 8a of a microbial detection container tool 1A placed on a loading portion, reflects the light which is detected by a sensor. An electronics signal from a sensor is converted by an A/D board from analog signal to digital signal and then is sent to a computer. The determination of microbial detection, data handling and data recording are done by a computer. Software algorithm is used for the determination of microbial detection and graphing techniques are used for displaying a result of detection. (Refer to FIG. 4(B)) The detection time is also being kept track by a computer. An alarm is activated by the microorganism detection signal from a sensor. Using a system, the process of microbial growth is measured, monitored and recorded and the presence of microorganisms is detected.

FIG. 1(B) shows second form of application of the present invention.

As FIG. 1(B) shows, a microbial detection container tool 1B is a transparent container 3b capable of keeping inside airtight by a cap 2b, inside of which a $CO_2$ gas-permeable membrane 4b isolates a $CO_2$ indicator portion 6b from a fluid culture medium portion 5b. The body of a container 3b only holds a fluid culture medium portion 5b. A cap 2b has a cylinder shaped part 9 that sticks out. A $CO_2$ indicator portion 6b is located inside of a cylinder shaped part 9. A $CO_2$ indicator portion 6b accommodates a $CO_2$ indicator 8b. A $CO_2$ gas-permeable membrane 4b encloses a cylinder shaped part 9 and holds a $CO_2$ indicator portion 6b inside of a cylinder shaped part 9. A $CO_2$ gas-permeable membrane 4b is made out of transparent polypropylene film and isolates a culture medium 7b supporting the growth of microorganisms. A microbial detection container tool 1B has the same function as a microbial detection container tool 1A does, which is described in the first form of application of the present invention.

FIG. 1(C) shows third form of application of the present invention.

As FIG. 1(C) shows, a microbial detection indicator tool 1C is a transparent bag of $CO_2$ gas-permeable membrane 4c which holds a $CO_2$ indicator 8c inside. A $CO_2$ gas-permeable membrane 4c is made out of transparent polypropylene and isolates a fluid culture medium containing a sample. A microbial detection indicator tool 1C has the same function as a microbial detection container tool 1A does, which is described in the first form of application of the present invention.

A microbial detection indicator tool 1C shown in FIG. 1(C) has simple structure, can be dipped into a culture medium containing a sample as it is, and can detect the presence of microorganisms by a color response of a $CO_2$ indicator 8c in the bag.

FIGS. 1(D), (E) show forth form of application of the present invention. As FIGS. 1(D), (E) show, a microbial detection container tool 1D is a transparent container 3d capable of keeping inside airtight by a cap 2d, inside of which a $CO_2$ gas-permeable membrane 4d isolates a $CO_2$ indicator portion 6d from a fluid culture medium portion 5d. The body of a container 3d has a fluid culture medium portion 5d. A cap 2d is made out of transparent material and its opening facing toward inside of a container is covered by a $CO_2$ gas-permeable membrane 4d. A $CO_2$ gas-permeable membrane 4d is made out of transparent polypropylene film and isolates a culture medium 7d supporting the growth of microorganism. A $CO_2$ indicator portion 6d is located in a space between a cap 2d and a $CO_2$ gas-permeable membrane 4d. In a $CO_2$ indicator portion 6d, a blotting paper 8d soaked up a solution of a $CO_2$ indicator is placed between a cap 2d and a $CO_2$ gas-permeable membrane 4d. A microbial detection container tool 1D has the same function as a microbial detection container tool 1A does, which is described in the first form of application of the present invention.

FIG. 1(F) shows fifth form of application of the present invention.

As FIG. 1(F) shows, a microbial detection container tool 1E is a transparent container 3e capable of keeping inside airtight by a transparent cap 2e, inside of which a $CO_2$ gas-permeable membrane 4e isolates a $CO_2$ indicator portion 6e from a fluid culture medium portion 5e. Both the inside of a cap 2e and the bottom of a container 3e have sticking out parts 2f and 3f respectively which face toward center of a container. A $CO_2$ gas-permeable membrane 4e is made out of a transparent polypropylene tube and isolates a culture medium 7e supporting the growth of microorganisms. Inside of a container 3e, each end of a $CO_2$ gas-permeable membrane tube 4e is connected into sticking out parts 2f and 3f on a cap 2e and on the bottom of a container 3e respectively. Either inner wall or outer wall of this tube shaped $CO_2$ gas-permeable membrane 4e is glued on to a cylinder shaped support which has many holes on its wall and is connected into sticking out parts 2f and 3f on a cap 2e and on the bottom of a container 3e, at the each end, respectively.

A fluid culture medium portion 5e is in a space between inner wall of a container 3e and outer wall of a $CO_2$ gas-permeable membrane tube 4e. A $CO_2$ indicator portion 6e is in a space inside of a $CO_2$ gas-permeable membrane tube 4e. A $CO_2$ indicator portion 6e contains a $CO_2$ indicator 8e.

Using a microbial detection container tool 1E shown in FIG. 1(F), the determination of microbial detection is accomplished by verifying a color response of a $CO_2$ indicator 8e located in a $CO_2$ indicator portion 6e, observing through the inside of a $CO_2$ gas-permeable membrane tube 4e from a circular window at the bottom of a transparent container 3e. A microbial detection container tool 1E has the same function as a microbial detection container tool 1A does, which is described in the first form of application of the present invention.

Figure 5:
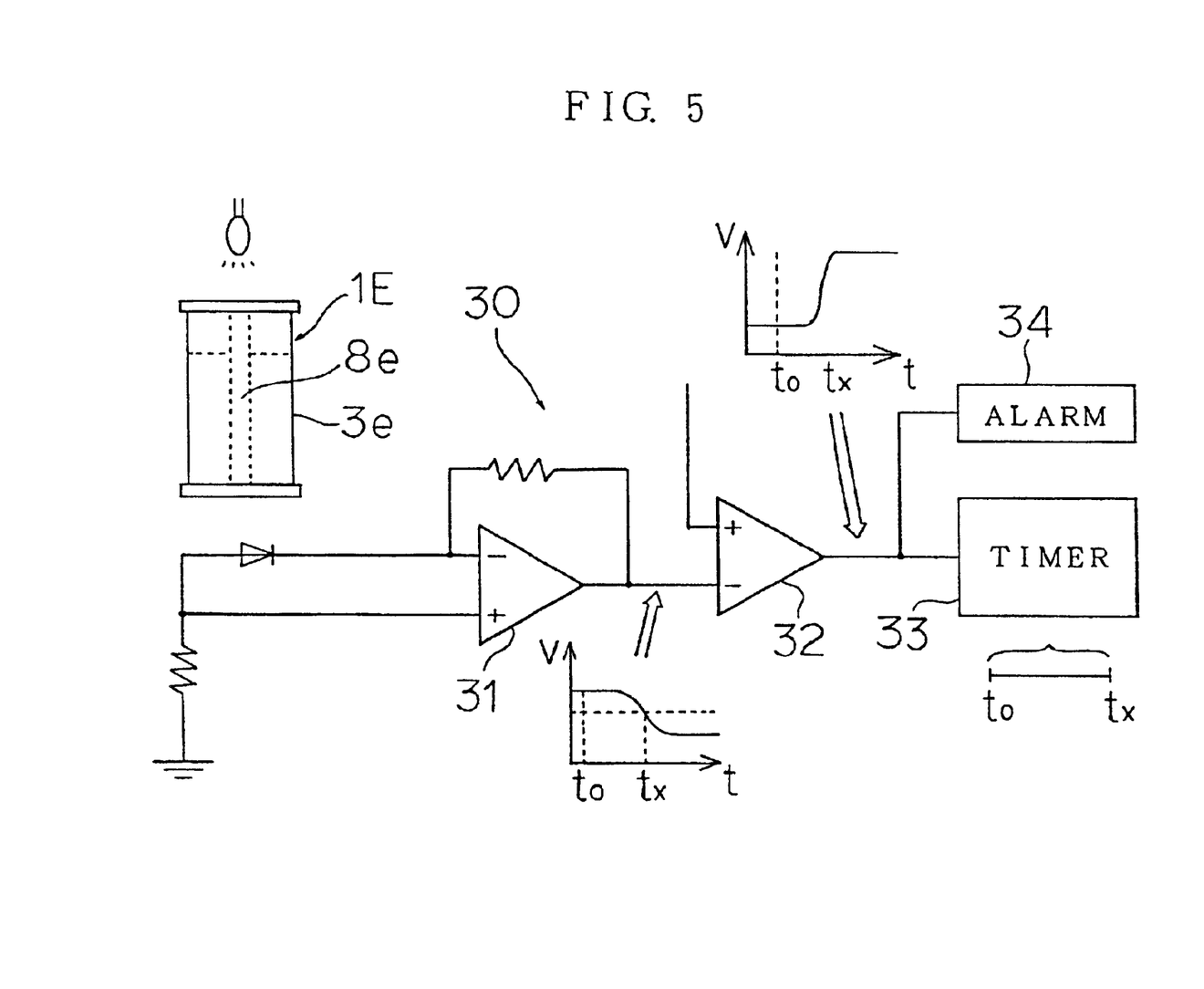

As FIG. 5 shows, a microbial growth time measuring system 20 using a microbial detection container tool 1E comprising a loading portion for a microbial detection container tool 1E, a sensor, analog amplifier circuits 31,32, a timer 33 and an alarm 34. A sensor monitors a color response of a $CO_2$ indicator 8e through the transparent bottom of a container 3e of a microbial detection container tool 1E placed on a loading portion, picks up the microorganism detection signal and sends it to a timer. A timer 33 comprising a stopwatch receives the microorganism detection signal from a sensor and measures the time from the moment when a container is loaded until the moment when the microorganism detection signal is received. An alarm 34 receives the microorganism detection signal from a sensor and sounds to inform the presence of microorganisms.

When a microbial growth time measuring system 20 is used, a container 3e is placed on a loading portion after a test sample is mixed in a culture medium 7e of a microbial detection container tool 1E and a container 3e is sealed. After a container is placed, an alarm 34 is cleared and a timer 33 is started. As a color of a $CO_2$ indicator 8e of a microbial detection container tool 1E starts to change as microorganisms grow, electronics detection signal changes according to a color response. Then, when the signal level crosses the threshold level, the microorganism detection signal becomes true, activating an alarm 34 and stopping a timer 33, as the presence of microorganisms is detected. By those operations, a timer 33 measures the time from the moment when a container is loaded until the moment when a sensor detects a color change of a $CO_2$ indicator 8e. The time shown by a timer 33 is the required time for microorganisms to grow and to reach to the detectable quantities. The quantities of microorganisms contained before being cultured is determined in a predictable fashion when the measured time is compared to those obtained using known quantities of the same microorganism species in known amount of test sample. Besides using an original sample, if samples of diluted by 10 times, 100 times and 1000 times are prepared and tested at the same time, the initial quantities of microorganism can be obtained more accurately.

A method for detecting microorganisms or a method for identifying quantities of microorganisms that uses a microbial detection tool 1A~1E, a microbial detection system 10, 20, or a microbial growth time measuring system 30, can be utilized for the following applications;

(1) sterilization test and quality control in industries: drink bottling industry, food processing industry, dairy product industry, meat and poultry industry, pharmaceutical industry, cosmetic industry, etc., (2) determining quantities of microorganisms in a test sample in general, (3) detecting specific species of microorganism by using selective culture medium, (4) research and analysis on growth process of microorganisms under different conditions, (5) testing antibiotic substance, (6) microbial detection on a blood sample in the medical field, (7) detecting coliform group or as such on a sample of ice/snow, soft drinks, powder material for drinks and so on, instead of using a Durham tube for microbial detection.

Note that the aforementioned disclosure claims the priority of and relates to the subject matter contained in Japanese Patent Application No. 9-365342 filed on Dec. 18, 1997, which is incorporated by reference in this application in its entirety.

What is claimed is:

1. A method for detecting presence of microorganisms in a sample, comprising the steps of:

(a) preparing a container comprising a medium portion which has a fluid culture medium for supporting growth of microorganisms and a fluid indicator isolated from the medium portion which contains a color changing $CO_2$ indicator for detecting the presence of mircoorganisms;

(b) wherein said fluid indicator portion is isolated from said medium portion by a $CO_2$ gas-permeable membrane, which permeates $CO_2$ gas at a pressure required to maintain a density of $CO_2$ gas at a level reccquired for growth of a microorganism;

(c) mixing a sample in said fluid culture medium;

(d) sealing said container entirely from outside atmosphere; and (e) indicating the presence of microorganisms by determining a color change of said $CO_2$ indicator.

2. A method for identifying quantities of microorganisms in a sample, comprising the steps of:

(a) preparing a container comprising a medium portion which has a fluid culture medium for supporting growth of microorganisms and a fluid indicator isolated from the medium portion which contains a color changing $CO_2$ indicator for detecting the presence of microorganisms;

(b) wherein said fluid indicator portion is isolated from said medium portion by a $CO_2$ gas-permeable membrane, which permeates $CO_2$ gas at a pressure required to maintain a density of $CO_2$ gas at a level required for growth of a microorganism;

(c) mixing a sample in said fluid culture medium;

(d) sealing said container entirely from outside atmosphere;

(e) measuring time, starting from a moment when said container is sealed until a moment when color of said $CO_2$ indicator is turned into a predetermined color; and (f) identifying initial quantities of microorganisms obtained by comparing measured time against contents of a table which holds pre-collected time data on each microorganism species of known initial quantities in known amount of sample.

3. A method for identifying quantities of microorganisms in a sample, comprising the steps of:

(a) preparing a container comprising a medium portion which has a fluid culture medium for supporting growth of microorganisms and an indicator isolated from the medium portion which contains a color changing $CO_2$ indicator for detecting the presence of microorganisms;

(b) wherein said indicator portion is isolated from said medium portion by a $CO_2$ gas-permeable membrane, which permeates $CO_2$ gas at a pressure required to maintain a density of $CO_2$ gas at a level required for growth of a microorganism;

(c) mixing a sample in said fluid culture medium;

(d) sealing said container entirely from outside atmosphere;

(e) measuring time, starting from a moment when said container is sealed until a moment when color of said $CO_2$ indicator is turned into a predetermined color; and (f) identifying initial quantities of microorganisms obtained by comparing measured time against contents of a table which holds pre-collected time data on each microorganism species of known initial quantities in known amount of sample.

* * * * *